(12) United States Patent
Wolff et al.

(10) Patent No.: US 8,815,264 B2
(45) Date of Patent: Aug. 26, 2014

(54) WATER-BASED OLEFIN-GRAFT POLYMER SYSTEM FOR MULTIFUNCTIONAL COSMETIC APPLICATIONS

(75) Inventors: Norwin W. Wolff, Marshfield Hills, MA (US); Timothy L. Martin, Louisville, KY (US); William Tenney, Medway, MA (US); Joseph J. Cincotta, Trumbull, CT (US)

(73) Assignee: Interpolymer Corporation, Canton, MA (US)

(*) Notice: Subject to any disclaimer, the term of this patent is extended or adjusted under 35 U.S.C. 154(b) by 325 days.

(21) Appl. No.: 11/713,457

(22) Filed: Mar. 2, 2007

(65) Prior Publication Data

US 2008/0031840 A1 Feb. 7, 2008

Related U.S. Application Data

(63) Continuation of application No. PCT/US2005/031214, filed on Sep. 1, 2005.

(60) Provisional application No. 60/606,985, filed on Sep. 3, 2004, provisional application No. 60/627,224, filed on Nov. 12, 2004.

(51) Int. Cl.
*A61K 8/02* (2006.01)
*A61K 8/81* (2006.01)
*A61K 8/00* (2006.01)

(52) U.S. Cl.
USPC .................. 424/401; 424/70.15; 510/119

(58) Field of Classification Search
None
See application file for complete search history.

(56) References Cited

U.S. PATENT DOCUMENTS

| | | | |
|---|---|---|---|
| 3,145,147 A | 8/1964 | Glickman et al. | |
| 3,932,610 A * | 1/1976 | Rudy et al. | 510/119 |
| 4,032,747 A | 6/1977 | Kunz | |
| 4,177,178 A | 12/1979 | Das et al. | |
| 4,196,190 A * | 4/1980 | Gehman et al. | 424/47 |
| 4,223,009 A | 9/1980 | Chakrabarti | |
| 4,501,834 A | 2/1985 | Su | |
| 4,506,454 A | 3/1985 | Kerschgens | |
| 4,521,404 A | 6/1985 | Lorenz et al. | |
| 4,543,249 A * | 9/1985 | Nelson | 424/70.16 |
| 4,710,374 A | 12/1987 | Grollier et al. | |
| 4,725,492 A | 2/1988 | Yazaki et al. | |
| 4,796,646 A | 1/1989 | Grollier et al. | |
| 4,874,604 A * | 10/1989 | Sramek | 424/47 |
| 5,009,880 A | 4/1991 | Grollier et al. | |
| 5,068,099 A | 11/1991 | Sramek | |
| 5,126,124 A | 6/1992 | Tazi et al. | |
| 5,185,143 A * | 2/1993 | Cohen | 424/47 |
| 5,441,728 A | 8/1995 | Tsaur et al. | |
| 5,501,851 A | 3/1996 | Mudge et al. | |
| 5,519,063 A * | 5/1996 | Mondet et al. | 514/772.4 |
| 5,686,062 A | 11/1997 | Tong | |
| 5,723,113 A | 3/1998 | Faryniarz et al. | |
| 5,874,069 A * | 2/1999 | Mendolia et al. | 424/65 |
| 5,948,396 A | 9/1999 | Das et al. | |
| 5,980,878 A | 11/1999 | Torgerson et al. | |
| 5,997,851 A * | 12/1999 | Cox et al. | 424/70.1 |
| 5,998,500 A | 12/1999 | Cahill et al. | |
| 6,136,296 A * | 10/2000 | Midha et al. | 424/47 |
| 6,294,158 B1 * | 9/2001 | Dupuis | 424/70.1 |
| 6,297,326 B1 | 10/2001 | Wang et al. | |
| 6,471,952 B1 * | 10/2002 | Dubief et al. | 424/70.12 |
| 6,482,394 B1 | 11/2002 | Schehlmann et al. | |
| 6,534,047 B1 | 3/2003 | Bodelin | |
| 6,696,050 B2 * | 2/2004 | Barbuzzi et al. | 424/70.11 |
| 2003/0012752 A1 * | 1/2003 | Bara | 424/63 |
| 2003/0012757 A1 * | 1/2003 | Barbuzzi et al. | 424/70.1 |
| 2003/0171246 A1 | 9/2003 | Boeckh et al. | |
| 2003/0180245 A1 * | 9/2003 | Gotsche et al. | 424/70.16 |

FOREIGN PATENT DOCUMENTS

| | | |
|---|---|---|
| EP | 0 581 264 A | 2/1994 |
| WO | WO 2006/028931 | 3/2006 |

OTHER PUBLICATIONS

Zviak, The Science of Hair Care, 1986, Marcel Dekker, p. 1-4.*
EP1319389, Machine Translation of Description, retrieved online on Sep. 7, 2011, p. 1-3.*
EP1092418, Machine Translation of Description, Retrieved online on Sep. 7, 2011, p. 1-4.*
International Search Report for PCT/US2005/007925, date of mailing Jul. 12, 2005.
Office Action from U.S. Appl. No. 12/313,012 dated Nov. 13, 2009.
Office Action from U.S. Appl. No. 12/313,012 dated Jun. 17, 2010.
EP1319389, Machine Translation of Description, Retrieved on Sep. 7, 2011, p. 1-3.
EP1092418, Machine Translation of Description, Retrieved on Sep. 7, 2011, p. 1-4.

(Continued)

*Primary Examiner* — Brian-Yong Kwon
*Assistant Examiner* — Jennifer A Berrios
(74) *Attorney, Agent, or Firm* — Hamilton, Brook, Smith & Reynolds, P.C.

(57) ABSTRACT

A polymer emulsion for use in a cosmetic composition includes an olefin copolymer; a copolymer of an acidic monomer to include acrylic acid, methacrylic acid or other unsaturated, carboxyl containing monomer; optionally, at least one stabilizing emulsifier; optionally, a resin selected from a group consisting of an acrylic resin and styrene-acrylic resin, said resin having an average molecular weight from about 500 to about 15,000 daltons; and, optionally, a polymer selected from a group consisting of oxidized polyethylene polymers and oxidized polypropylene polymers, said polymer modified with cationic end-groups such as tallow alkyl amines.

18 Claims, 4 Drawing Sheets

(56) References Cited

OTHER PUBLICATIONS

Final Office Action from U.S. Appl. No. 12/313,012, dated Oct. 12, 2011.
International Search Report in International Application No. PCT/US2005/031214, entitled "Acryl-Grafted Olefin Copolymer Emulsions for Multifunctional Cosmetic Applications," 3 pages, date of mailing: Jul. 3, 2006.
International Preliminary Report on Patentability in International Application No. PCT/US2005/031214, entitled "Acryl-Grafted Olefin Copolymer Emulsions for Multifunctional Cosmetic Applications," 7 pages, date of issuance: Mar. 6, 2007.
Office Action dated Nov. 20, 2012 in U.S. Appl. No. 12/313,012.
Office Action, U.S. Appl. No. 12/313,012, "Water-Based Olefin-graft Polymer System for Multi-Functional Cosmetic Applications." Date of mailing: Apr. 15, 2013.

\* cited by examiner

WATER-BASED OLEFIN-GRAFT POLYMER SYSTEM FOR MULTIFUNCTIONAL COSMETIC APPLICATIONS

RELATED APPLICATIONS

This application is a continuation of PCT/US2005/031214, filed on Sep. 1, 2005, which claims the benefit of U.S. Provisional Application No. 60/606,985, filed on Sep. 3, 2004 and of U.S. Provisional Application No. 60/627,224, filed on Nov. 12, 2004. The entire teachings of the above applications are incorporated herein by reference.

BACKGROUND OF THE INVENTION

There is a need in a stable polymer emulsion having multifunctional capabilities for use on keratinous surfaces.

SUMMARY OF THE INVENTION

The present invention relates to the olefin-graft polymer providing a combination of one or more of the following attributes to cosmetic formulations: hair fixative properties, thermal restyling, color retention properties, volumizing and texturizing properties and sun protection factor (SPF) boosting.

In one embodiment, the present invention is a polymer emulsion for use in a cosmetic composition. The polymer emulsion comprises an olefin copolymer and a copolymer of acrylic and/or methacrylic acid and/or other unsaturated acidic monomers.

In another embodiment, a polymer emulsion of the present invention can comprise an olefin copolymer; a copolymer of acrylic acid and/or methacrylic acid and/or unsaturated acidic monomer; at least one stabilizing emulsifier; a resin selected from a group consisting of an acrylic resin and styrene-acrylic resin, said resin having an average molecular weight from about 500 to about 15,000 daltons; and a polymer selected from a group consisting of oxidized polyethylene polymers and oxidized polypropylene polymers, said polymer manufactured with cationic groups.

In another embodiment, the present invention is a method of fixing hair, comprising contacting hair with a composition comprising a polymer emulsion of the present invention.

In another embodiment, the present invention is a method of thermally restyling hair. The method comprises contacting hair with a composition comprising a polymer emulsion of the present invention; heating hair; and styling the heated hair.

In another invention, the present invention is a method of cleaning hair. The method comprises contacting hair with a cleaning composition comprising a polymer emulsion of the present invention and rinsing the hair.

In another embodiment, the present invention is a method of protecting skin from ultraviolet radiation. The method comprises contacting skin with a composition comprising a polymer emulsion of the present invention.

In another embodiment, the present invention is a personal care fixative comprising a polymer emulsion of the present invention.

In another embodiment, the present invention is a method for fixing a keratin-type structure. The method comprises the step of applying the personal care fixative that comprises a polymer composition of the present invention to the keratin-type structure.

This multi-functional capability can be attributed to the unique balance of low functional, semi-crystalline olefin activated by higher functional, amorphous acrylic polymer chains. This balance provides for a unique blend of properties as described in this patent. The olefin-graft polymers of this invention can be used in both hair care applications and skin protection.

DETAILED DESCRIPTION OF THE INVENTION

Figure 1:
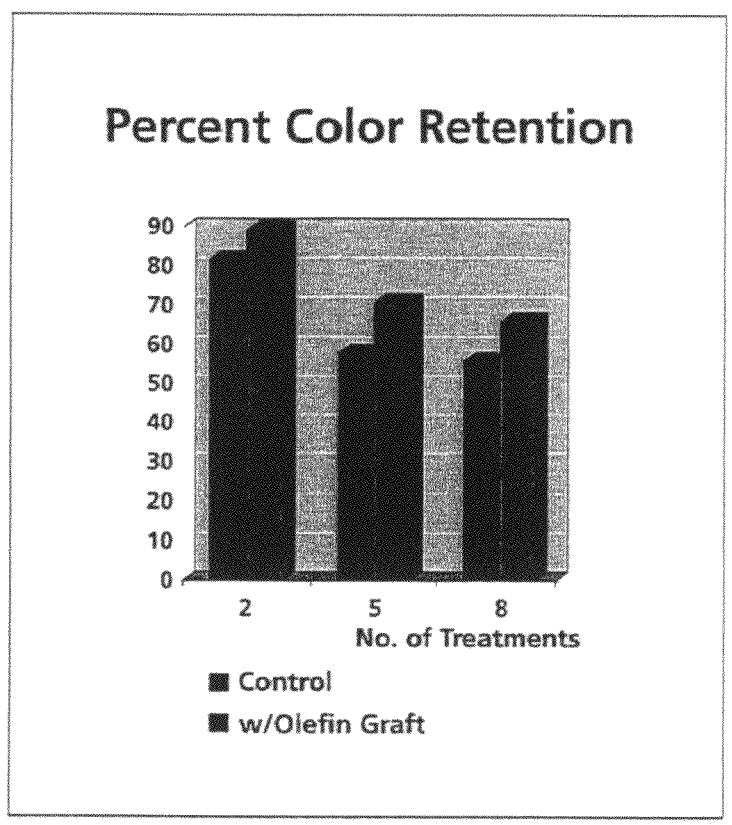
FIG. 1 is a bar plot of percent color retention as a function of number of treatments with a conditioner. Color-treated hair was subjected to treatment by a conditioner comprising a composition of the present invention as well as by a control formulation.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

The present invention is a stable emulsion for use in a cosmetic composition. The emulsion of the present invention comprises the following components:

(1) A semicrystalline olefin copolymer. The semi-crystalline olefin copolymer can include two or more of the following monomers: ethylene, propylene, acrylic acid, methacrylic acid, melaic anhydride, crotonic acid, vinyl acetate, ethyl acrylate and similar lower C1-C8 esters of acrylic and methacrylic acid;

(2) A copolymer of acrylic acid and/or methacrylic acid and/or unsaturated acidic monomer. The copolymer of the acidic monomer can include one or more of the following monomers: ethyl acrylate, butyl acrylate, 2-ethyl hexyl acrylate, butyl methacrylate, methyl methacrylate, styrene, an ethoxylated C1-C6 ester of acrylic and methacrylic acid such as hydroxpropyl methacrylate, hydroxyethyl methacrylate, hydroxylethyl acrylate, polyethylene glycol (PEG) and polypropylene glycol (PPG) modified acrylates and methacrylates with 1-10 moles of ethylene oxide or propylene oxide or combination of both. The copolymer of acrylic acid can further include one or more of the following monomers: the lower amino alkyl (C1-C6) esters of methacrylic and acrylic acid, such as dimethylaminoethyl methacrylate, diethylaminoethyl methacrylate, t-butylaminoethyl methacrylate, dimethyldiallylmethacrylate as well as their quaternized adducts.

A composition of the present invention can further optionally include the following components:

(3) One or more stabilizing emulsifiers. Stabilizing emulsifiers for the purpose of this invention are described as any emulsifier containing a combination of lipophilic and hydrophilic segments capable of forming oil in water emulsions and has the ability to maintain the integrity of the emulsion over extended time periods. The stabilizing emulsifiers can be any anionic surfactant suitable for emulsion polymerization techniques. General techniques associated with emulsion polymerization suitable for practicing the present invention are discussed in D. C. Blackley, Emulsion Polymerization (Wiley, 1975). The teachings of this publication are incorporated herein by reference in their entirety. Non-limiting examples of stabilizing emulsifiers include sodium lauryl sulfate, sodium lauryl ether sulfate, sulfonated mono and dialkyl esters of succinic acid and their salts, alkyl esters of diphenyl oxide. Stabilizing emulsifiers can further be selected from non-ionic emulsifiers such as C10-C30 alkyl alcohol ethoxylate and ethylene oxide-propylene oxide block polymers.

(4) Acrylic or styrene-acrylic resins of an average molecular weight from 2000 to 15,000 daltons. The monomers of these resins can be selected from the monomers listed with reference to components (1) and (2) above. These resins are believed to improve mechanical performance properties of the composition of the present invention.

(5) Oxidized polyethylene or polypropylene polymers manufactured with cationic functionality such as but not limited to tallow alkyl amines. An example of a suitable tallow alkyl amine is Aquacer 840™ from BYK Cera®. It is believed that component (5) can improve hydrophobic/hydrophilic balance and improve substantivity of the composition of the present invention.

In the final composition, in percent by weight, component (1) can be present from 30% to 99%; component (2) can be present from 1% to 70%; component (3) can be present from 0 to 15%, preferably from 1 to 15%; component (4) can be present from 0 to 20%, preferably from 0.2% to 20%; and component (5) can be present from 0 to 5%, preferably from 0.5% to 1.5%.

Preferably, final compositions of this invention have an average molecular weight in the range of 500-1,000,000 daltons. Particle size of polymers of this invention has a range from 10 to 250 nm with a Minimum Film Formation Temperature (MFT) of −10 to 70° C. but most preferably between 0 and 30° C.

As used herein, the term "semicrystalline polymer" refers to polymers that exist as viscous liquids at temperatures above the melting point of the crystals. Upon cooling, crystals nucleate and grow to fill the available volume. The reason these materials are called "semicrystalline" is that some fraction of the polymer remains un-crystallized, or, amorphous when the polymer is cooled to room temperature. The amorphous polymer becomes trapped between the growing crystals. As a result of the highly entangled nature of the polymer chains, the movement of the amorphous polymer becomes restricted.

As used herein, the term "olefin" refers to an alkene. The term "alkene", as used herein, refers to any aliphatic hydrocarbon whose molecules contain one or more carbon-carbon double bonds.

An "alkyl group," as the term is used herein, is a hydrocarbon in a molecule that is bonded to one other group in the molecule through a single covalent bond from one of its carbon atoms. Alkyl groups can be cyclic, branched or unbranched, substituted or unsubstituted, and/or saturated or unsaturated. An alkyl group can have, for example, 1 to about 24 carbons atoms, 1 to about 12 carbon atoms, or about 1 to about 4 carbon atoms, e.g., methyl, ethyl, n-propyl, iso-propyl, n-butyl, sec-butyl and tert-butyl.

Manufacture of the polymers of this invention can be accomplished via the following procedure. Semi-crystalline olefin polymers are commercially available from various suppliers such as Honeywell, Dupont and Sud-Chemie. Polymers of this type are supplied in a pellet or flake form and must be emulsified before use. Depending on the functionality of the base olefin, this may be accomplished with or without pressure. Higher melting olefins and lower functionality polymers require more heat and a pressure vessel to emulsify. Specific emulsification procedures for these polymers are supplied by the individual suppliers and are not required for description for this invention. In general, the process involves the melting of the polymer pellet above its softening/melting point in the presence of an adequate neutralizing base to provide adequate emulsion stability in the water phase.

Grafting as described in this invention describes the physical entanglement of polymer chains and covalent grafting. Grafting is sufficient to provide a uniform polymer emulsion with a single Glass Transition Temperature ($T_g$) and an ability to withstand thermal and chemical attack without dissociation.

The invention is further described by the following examples, which are not intended to be limiting in any way.

EXEMPLIFICATION

Example 1

Preparation of an Exemplary Composition of the Present Invention

An exemplary composition of the present invention was prepared using the ingredients listed in Table 1.

TABLE 1

Olefin-graft Composition 1.

| Material | Weight Percent/wet |
|---|---|
| (Part A) | |
| Ethylene/Methacrylic Acid Copolymer | 17.9 |
| Water | 35.8 |
| 2°Alcohol Ethoxylates@ 83% | 3.1 |
| Alcohol Ethoxylate @ 100% | 0.2 |
| Sodium laureth sulfate @ 30% | 1.8 |
| Potassium Hydroxide Flake | 0.4 |
| (Part B) | |
| Water | 28.3 |
| Acrylic Resin (Mw 6000) @ 25% | 2.2 |
| Sodium Deceth-6 Sulfosuccinate @ 30% | 0.8 |
| Sodium Persulfate | 0.18 |
| t-Butyl Hydroperoxide | 0.02 |
| Water | 0.9 |
| Sodium Metabisulfite | 0.4 |
| 2-ethyl hexyl acrylate | 3.1 |
| t-butylaminoethyl methacrylate | 2.0 |
| dimethylaminoethyl methacrylate | 1.0 |
| butyl acrylate | 1.1 |
| hydroxyl propyl methacrylate | 0.8 |
| Total: | 100.0 |

All the ingredients listed in Part A were combined in a pressure vessel and heated. The mixture was heated under agitation until a temperature of 130° C. and held under pressure and agitation for one hour. Next, the mixture was rapidly cooled with either an external ice bath or internal coil to less than 100° C.

When the temperature has fallen below 100° C. and Part B was added in the order listed. The temperature was maintained between 80-100° C. until monomer conversion was complete with residual monomer levels less than about 5.0 ppm as determined by Gas Chromatograph headspace analysis.

The mixture was cooled and polymer was checked. Polymer solids were found at 30% n.v.; pH=9.6; viscosity=40 cps.

Example 2

Thermal Restyling of Hair

One of the unique characteristics of the composition of the present invention is its elasticity under mild heat conditions as produced by a typical consumer hair dryer. Tests utilizing dried films of a polymer of this invention were made to determine the degree of elasticity of the film under mild heating.

Films of Example One were prepared by drying a one mil film of the polymer on glass. The film was then mechanically removed using a sharp blade. Cut films approximately 1 cm×4 cm in size were stretched between a fixed anchor point and a mechanical pulley assembly with light twine connecting the film to the pulley system. The distance between the anchor points was fixed at 10 mm. The films were stretched by gently tightening the pulley system until the film reached a point of failure or total breakage. The distance stretched was recorded and compared to the original test length to calculate the percent elongation. Baseline films were tested at ambient conditions of 73° F. and 45% relative humidity.

In order to determine the effect of heat, a consumer hair dryer was used to direct a flow of hot hair on the films while the film was tested via the pulley system. The dryer was set on a low setting resulting in an air temperature of 140° F. Again the films were stretched via the same method with the results shown in Table 2.

TABLE 2

|  | Average Ambient Test Measurement | Average Heated Test Measurement |
|---|---|---|
| One Mil Film/10 mm starting width | 13 mm | 53 mm |
| Percent Elongation | 30% | 530% |

In order to determine the effectiveness of this specific trait as it pertains to hair, the following test was performed at 72° F. and 42% relative humidity. Standard hair tresses from International Hair Importers were washed and dried with a consumer shampoo and allowed to dry overnight. (Hair tresses are 25 cm in length before curling.) Half of the samples were rewet and then treated with 5 milliliters of a 4% polymer solution 80% of the solution was of the type described in Example One, the remaining portion was a fixative resin from Interpolymer Corporation—Syntran PC5100. These tresses were also allowed to dry overnight. All tresses were then curled using a consumer curling iron set on high. The tresses treated with the polymer solution were placed horizontally and allowed to cool. The remaining tresses were sprayed with a commercially available fixable hold hair spray and then placed horizontally to dry and cool. The tresses were measured and hung vertically and measured again. All of the tresses were measured on an hourly basis for four hours. At the end of the test period, the hair tresses were stressed by combing out the curl 5 times with a wide toothed comb. Again the tresses were measured for curl retention. The curls were allowed to hang for another hour and then re-measured. In order to determine if the hair could be restyled without the addition of more hair fixative, the tresses were again curled with the consumer curling iron and measured. Again the curls were measured on an hourly basis for two more hours to represent an eight hour day. The results of the eight hour test are presented in Table 3.

TABLE 3

| Intervals and Tests | Invention Embodiment | Consumer Hair Spray |
|---|---|---|
| Initial Horizontal Measurement | 13.5 cm | 8.0 cm |
| Initial Vertical Measurment | 14.0 | 8.0 |
| One Hour | 14.0 | 8.0 |
| Two Hours | 14.0 | 8.0 |
| Three Hours | 14.0 | 8.0 |
| Four Hours | 14.0 | 8.0 |
| Post 5X Stress | 13.5 | 12.5 |
| One hour Post Stress | 13.5 | 13.0 |
| Restyle Measurement | 13.0 | 10.5 |
| One hour Restyle | 13.0 | 11.5 |
| Two hour Restyle | 13.0 | 12.5 |
| Final 8 hour Curl Retention | 109% | 73.5% |

This example illustrates that the composition of the present invention retains its ability to hold styling after stress and restyle while a commercial spray can not without re-application. The commercial spray appears to hold a tighter initial curl but can not maintain the curl after stress. The restyled tresses with the polymer solution demonstrated an even tighter curl after restyling than the initial curl.

Example 3

Texturizing Shampoo Comprising a Composition of the Present Invention

This shampoo with rich, thick lather not only cleanses hair but volumizes and texturizes fine limp hair. The composition of the present invention surrounds and supports each strand to give root-lift, manageability and excellent shine to lifeless hair. This texturizing shampoo formula adds style-support and texture while leaving hair with a clean, natural feel.

The texturizing shampoo was prepared from the ingredients listed in Table 4.

TABLE 4

|  | INCI Designation | Weight % |
|---|---|---|
| Phase A |  |  |
| Distilled Water |  | 43.00 |
| Dissolvine Na2—S (Akzo Nobel) | Disodium EDTA | 0.10 |
| Steol CS-230 (Stepan) | Sodium Laureth Sulfate | 16.00 |
| Stepanol AM (Stepan) | Ammonium Lauryl Sulfate | 14.00 |
| Amphosol HCG (Stepan) | Cocamidopropyl Betaine | 8.00 |
| Tauranol I-78 C (Finetex) | Sodium Cocoyl Isethionate | 5.00 |
| Mackamide CMA (McIntyre) | Cocamide MEA | 1.00 |
| Crothix (Croda) | PEG-150 Pentaerythrityl Tetrastearate | 0.25 |
| Glycol Stearate | Glycol Stearate | 0.50 |
| Phase B - add at 60° C. |  |  |
| Example 1 polymer |  | 6.00 |
| SYNTRAN PC 5100 | Styrene/Acrylates/Ammonium Methacrylate Copolymer | 1.50 |

TABLE 4-continued

| | INCI Designation | Weight % |
|---|---|---|
| Ritapan DL (RITA) | Panthenol | 0.75 |
| SYNTRAN PC 5320 | Polyquaternium-37 (Pending) | 2.00 |
| Fancorsil LIM-1 (Fancor) | Dimethicone PEG-8 Meadowfoamate | 1.00 |
| Phase C - add at 40° C. | | |
| Germall Plus (ISP) | Diazolidinyl Urea and IPBC | 0.35 |
| Fragrance | Fragrance | 0.30 |
| Citric Acid | Citric Acid | 0.08 |
| NaCl | NaCl | q.s. |
| YIELD: | | 99.83% |

The texturizing shampoo was prepared as follows. Phase A ingredients were heated to 75° C. When phase A became homogenous, it was cooling to 60° C. Phase B ingredients were added at 55°-60° C. and stirred until homogenous (no particles formed). The mixture was cooled to 40°-45° C. at which time phase C was added. The final adjustment for viscosity was performed using the NaCl. The mixture was cooled to room temperature with cold water and pH was adjusted to between 5.5-6.5.

Panel evaluation of hair tresses washed with the shampoo gave superior performance attributes in physical and tactile evaluations when compared to a consumer shampoo making the same styling and performance claims of texturizing and styling. Panel results are found in Table 5 based on the scale from 1 (poor) to 5 (excellent).

TABLE 5

| Parameter | Formula #1 Shampoo | Commercial Texturizing Shampoo |
|---|---|---|
| WET | | |
| Wet Application | 5 | 4/5 |
| Wet Combing | 4 | 3/4 |
| Wet Detangling | 4 | 2 |
| Residual Wet Feel | 3/4 | 3/4 |
| DRY | | |
| Initial Hold | 5 | 5 |
| Curl Character | 5 | 5 |
| Shine | 4/5 | 4/5 |
| Naturalness of Hold | 5 | 6 |
| Dry Residual Feel | 5 | 5 |
| Stiffness | 5 | 6 |
| Dry combing | 5 | 3/4 |
| Hold (comb 5x) | 4/5 | 3/4 |
| Frizz | 4/5 | 3 |
| Tactile Smoothness | 4 | 4 |
| Static/Flyaway | 4 | 3 |

Example 4

Curl Retention by Hair Treated by the Composition of the Present Invention

Compositions of this invention also display an ability to function as hair fixatives since they have a unique balance of hydrophobic and hydrophilic polymer segments. In order to determine the effectiveness of the curl retention properties, the following protocol was used to compare the olefin graft polymers to commercially available and commonly used hair fixative resins.

Tress Preparation

Prepare several Virgin hair tresses from International Hair Imports measuring 1.5 inch×6.5-7 inch (from same lot of hair). Wash each tress thoroughly with a strong detergent to remove any residual materials. Blot tresses with towel to remove excess water. Carefully comb through tress (starting at tip end) to remove tangles, snarls and knots. Do not excessively stretch hair in this process. Blot tress again if necessary so no free water exists.

Secure or clamp the plastic (root) end of the tress. Do not allow tresses to dry prior to application of test product.

Solution Application

Weigh 0.6 grams of the test solution into a disposable pipette (7 ml plastic transfer pipette is best). Slowly dispense approximately one-half the solution on several parts of the flattened tress. Squeeze top of tress between middle and index fingers and gently pull through tress to spread liquid through hair. Repeat with remainder of test solution. Care must be taken to get all material on hair (no dripping). If tress is especially dense you may use another 0.2 grams of test solution. However you then must remain consistent with this amount with other tresses.

Comb through tress once with fine end of comb to distribute solution and even out tress. While still clamped at plastic end, begin rolling tips of hair about a ¾-1 inch curling rod. It is not necessary to apply much tension. Wrap each rod with similar level of tension applied. The rods should have a clamping mechanism to secure rolled tress to rod. Let rolled tresses dry overnight in air at room temperature.

Very carefully remove dry hair from the curling rod. Make sure ends are dry; do not allow any water to come in contact with the hair. Manipulate tress with middle and index fingers if necessary to get curl back to proper configuration to conform to rod.

Hang tress on calibrated board and take initial reading at bottom of curl. Place curled hair in humidity chamber and note position of bottom of curl at prescribed time intervals. The duration of test may be as high as 5 hours.

Gel Application

Prepare and wash tresses as above. Weigh 0.5 grams (more if needed) of gel directly into a weigh boat. Using the index finger to scoop product and the middle finger to help spread, apply product to damp, detangled, clamped tress. Spread product as evenly through tress as possible. Comb through tress (1×) with fine end of comb to even out tress and help distribute product. Roll on curling rod as above. Let dry overnight at room temperature in air.

Curl retention was computed according to the following formula:

$$\text{Curl Retention} = (\text{Original Hair length} - \text{Test Curl Length})/(\text{Original Hair length} - \text{Original Curl Length}) \times 100$$

Two industry benchmark texturizing gel formulation were used as control in this experiment. The compositions of the control formulations are given below.

Formulation JC I/13 @3% N.V.
(All polymers were added so that final % solids=3%)

| | INCI Designation | Weight % |
|---|---|---|
| Phase A | | |
| Distilled Water | | 60.00 |
| Natrasol 250HHR-CS (Hercules) | Hydroxy Ethyl Cellulose | 1.00 |

-continued

| | INCI Designation | Weight % |
|---|---|---|
| Phase B | | |
| Distilled Water | | 30.01 |
| Disolvine Na2S (RITA) | Sod. EDTA | 0.07 |
| Ritapan DL (RITA) | Panthenol | 0.10 |
| Glycerin USP 99.7% (Witco) | Glycerin | 0.10 |
| Mackstat DM (McIntyre) | DMDM Hydantoin | 0.40 |
| Phase C | | |
| Brij 98 VEG (Uniqema) | Oleth-20 | 0.35 |
| Fragrance | Fragrance | 0.07 |
| Example 1 Polymer | | 7.90 |

Preparation procedure:
Hydrate Natrasol in water, heat to 45-50°. Mix until homogenous and clear.
Premix Phase B, heat to 35-40° C.
Melt Brij 98, add Fragrance. Add Phase C to Phase B. Stir until homogenous and clear. Add Polymer Example to Phase B/Phase C.
Add Phase B/Phase C to Phase A. Stir until homogenous.
Appearance: White, opaque - low viscosity gel. pH 8.28

Formulation JC I/24 @7% N.V.

(all polymers were added so that % solids were =7%)

| | INCI Designation | Weight % |
|---|---|---|
| Phase A | | |
| Distilled Water | | 80.12 |
| Phase B | | |
| Ritapan DL (RITA) | Panthenol | 0.10 |
| Lexaine C (Inolex) | Cocamidopropyl Betaine | 0.30 |
| Protaquat CT-29 (Protameen) | Cetrimonium Chloride | 0.10 |
| Promois WG-SIG (RITA) | Hydrolyzed Wheat Protein | 0.05 |
| | PG Propyl Methylsilanediol | 0.05 |
| Promois WG (RITA) | Hydrolyzed Wheat Protein | |
| Mackstat DM (McIntyre) | DMDM Hydantoin | 0.40 |
| Phase C | | |
| Brij 98 VEG (Uniqema) | Oleth-20 | 0.35 |
| Fragrance | Fragrance | 0.07 |
| Example 1 Polymer | | 18.42 |
| Citric Acid | Citric Acid | .04 |
| YIELD: | | 100.00% |

Preparation procedure:
Add water to vessel and heat to 35° C.
Add each Phase B ingredient. Stir between each addition until homogenous solution.
Melt Brij 98, add Fragrance (Phase C).
Add Phase C to Phase A/B. Stir until clear. When clear, add Example 1 Polymer.
Appearance: White, opaque liquid. pH 8.78. Add citric acid 0.12 g pH = 8.25.

Results of curl retention tests are presented in Table 6.

TABLE 6

| Texturizing Gel with Example 1 JC I/13 | Texturizing Gel with Luviquat JC I/25 | Styling Lotion with Example 1 JC I/24 | Styling Lotion With Amphomer JC I/23 | |
|---|---|---|---|---|
| 3.8 | 4.4 | 4.3 | 3.8 | Initial Curl Length |
| 6.8 | 8.0 | 6.3 | 6.3 | Final Curl Length |
| 95.1 | 94.9 | 97.2 | 97.8 | One Hour |
| 92.6 | 89.8 | 93.8 | 96.2 | 2 hours |
| 91.2 | 85.8 | 91.5 | 96.7 | 3 hours |
| 85.2 | 82.4 | 89.3 | 96.7 | 4 hours |
| 83.5 | 79.5 | 88.7 | 95.1 | 5 hours |

TABLE 6-continued

| Texturizing Gel with Example 1 JC I/13 | Texturizing Gel with Luviquat JC I/25 | Styling Lotion with Example 1 JC I/24 | Styling Lotion With Amphomer JC I/23 |
|---|---|---|---|
| Average Temp.: 85.5° F. | | Average Humidity 95% | |

Notes:
Amphomer ™, generic is Octylacrylamide/Acrylates/Butylaminoethyl Methacrylate Copolymer Luviquat ™, generic name is Polyquaternium-46.

Example 5

Retention of Color by Colored Hair When Treated by the Composition of the Present Invention Background By properly selecting olefin backbone and acrylic side chain of a graft polymer used in a composition of the present invention, functional groups can be attached to provide properties useful in a personal care product that heretofore were not easily achieved by an individual component.

Olefins are naturally semi-crystalline and provide features such as barrier and moisture retention, a reversible heat-activated elasticity and lubricity. This portion we designate as the Crystalline Polymer Portion or CPP. The acrylic side chains of this particular invention can range from soft and non-tacky to hard and brittle. The side chains may also contain amino functionality. For ease of nomenclature, we call the acrylic side chain portion of the composition the Amorphous Polymer Portion or APP. The APP contributes better film formation, adhesion, substantivity and stability to the olefin.

One possible structure of polymers of this type involves the bonding and entangling of styrene or acrylic polymers within the olefin polymeric layers, much like a sandwich. This is assisted by the acrylic chains' higher degree of flexibility than that of the semi-crystalline olefin. Depending on where this grafting interaction occurs, the olefin section will affect the conformation of the styrene/acrylic portion. By proper control of the hydrophilic/hydrophobic balance, it is possible to obtain a film with good acrylic, substantive properties while maintaining the olefin's barrier properties.

Color Treatment/Mechanism of Action

Hair coloring products work in different ways depending upon the level of coloring desired. These have been described by the industry as Level 1, semi-permanent color; Level 2, demi-permanent color and Level 3, permanent color. Each increasing level involves the additional use of chemicals to alter the color composition of the hair.

Level 1 colors do not appear to dramatically affect the natural color of the hair since the color molecules that enter the cuticle do not interact with the hair's natural pigment.

Level 2 colors appear to use a small amount of peroxide in order to enhance color but, unlike Level 3, they do not contain ammonia. During dyeing the Level 2 pre-color molecules penetrate the cuticle and enter the cortex where they partner to create medium sized molecules. These larger size molecules retard or prevent the degradation process of color fading.

Finally, Level 3 colors use both ammonia and peroxide to lighten the hair's natural pigment, in addition to adding a new permanent color. The ammonia can cause the cuticle to swell allowing the color precursor to enter the cortex. The precursors react and expand to a size to which they can not easily be washed out. The final color is a combination of the natural color and the new shade chosen.

For this experiment, we chose to use Level 2 colors which provided more dramatic and easily measurable distinctions between wash cycles. If the tested products in question performed in limiting dye loss during washing the Level 2 colorants, then we felt confident that these results would also translate well for Level 3 colors. The color loss of Level 2 colorants during hair washing cycles can be partially attributed to anionic and amphoteric shampoo ingredients which can draw oppositely charged dye molecules from the hair cortex through the openings in the hair cortex. This gradual leaching of the color molecules through the openings in the cuticle is the primary cause of color loss at this level. UV degradation is another means of color loss and is not being addressed by this process but can be mollified by the use of UV absorbers which are known to the industry. This is a particular problem with Level 3 colors.

Olefin graft polymers appear to work as occlusive barriers but contain both anionic and cationic charges which can serve to limit shampoo interaction with most dye molecules. As mentioned above, olefin graft polymers can provide substantivity to the hair shaft via the acrylic portion and use the crystalline olefin portion to occlude the cuticle openings limiting color loss.

Objective

One property demonstrated by the compositions of this invention is the ability to effect the hair cuticle during oxidative dying of the hair. By providing for an occlusive block to prevent the migration of dye molecules, these polymers can influence the amount of color loss or gain during the dying process and during shampoo maintenance. For this study, we chose to use Level 2 colors which provided more dramatic and easily measurable distinctions between wash cycles.

The following protocol was used for hair preparation and coloring.

Material List:
  Bleached blonde human hair was obtained from International Hair Importers and Products (IHIP) of White Plains, N.Y. The hair was swatched by Interpolymer Corporation and secured with wound wire and rubber cement. Each tress was three (3) grams in net weight before tressing and was six inches in length.
  A Level 2 commercial oxidative dye (Dark Brown) was used to treat the hair.
  The shampoo chosen was a commercial shampoo for normal hair with no color retention claims.
  A laboratory prepared leave-in conditioner using an olefin graft polymer was used. (see below formula)
  A laboratory prepared control leave-in conditioner without a graft polymer was used.

Leave-in Conditioner with 5% Olefin Graft Polymer

|  | Weight Percent |
|---|---|
| Phase A | |
| Distilled Water | 87.93 |
| Disodium EDTA | 0.05 |
| Propylene Glycol | 1.50 |
| Panthenol | 0.30 |
| PG-Hydroxyethylcellulose Cocodimonium Chloride | 2.50 |
| Cetrimonium Chloride | 0.75 |
| Polyquaternium-59 (and) butylene glycol | 1.00 |
| Phase B | |
| DMDM Hydantoin | 0.40 |
| Hydroxypropyltrimonium Hydrolyzed Silk | 0.10 |
| Hydrolyzed Silk | 0.05 |

-continued

|  | Weight Percent |
|---|---|
| Phase C @45° C. | |
| Oleth-20 | 0.35 |
| Fragrance | 0.07 |
| Phase D | |
| Polymer of Example 1 | 5.00 |
| Citric Acid | Q.S. |

Water was warmed to 35° C. Each ingredient was added as listed. The mixture was stirred between each addition addition until clear, producing a homogenous solution.

Phase C was added at 45° C. and stirred until clear. Next, Phase D was added and pH was adjusted with diluted citric acid to pH of 5.5-6.0.

The following evaluation procedure was employed.

Each tress was washed and rinsed before treating with the color to eliminate any contamination from the tress preparation. A minimum of 5.5 grams of the hair color was applied to the hair tress and spread evenly and thoroughly on both sides of the tress using a wide coloring brush and fingers. The tresses were allowed to process on aluminum foil for the manufacturer's recommended time at ambient temperature, approximately 23° C. The tresses were then rinsed with running tepid water for two minutes. The tresses were then allowed to dry for a minimum of two days before testing began.

The color hair were subjected to the following treatment cycle:
  1. Shampoo: Wet tress and apply two (2) grams of shampoo. Spread the shampoo evenly through the tress and then massage between the fingers from top of tress to bottom five times to create a lather. Rinse with tepid water until free of soap, approximately 15 seconds. Squeeze out the excess water using the middle and index finger and proceed.
  2. Conditioner: Apply two grams of conditioner formula (test or control) is applied to the wet tress and allowed to rest for one minute. Comb the tress with a wide tooth comb to remove excess conditioner and then dried.
  3. Drying: Oven dry the swatches for one hour at 35 C.

The above cycle was repeated Eight (8) times, with measurements taken at intervals of 2, 5 and 8. The hair samples were then evaluated for color loss using a Series Sphere Spectrophotometer, X-Rite Model SP-62. L*, a*, and b* values are measurements of color on a 3-D grid. Finally color retention, expressed as a percent, was calculated by determining the Delta E value representing the color shift along the three color coordinates after each treatment interval. Delta E values were correlated using an undyed hair standard and dyed hair with no treatment standard.

Initial results showed approximately 15% improvement in color retention with the olefin graft conditioner over the control conditioner over a period of 8 wash and condition cycles. These results are presented in FIG. 1.

A second round of tests were conducted. Modifications were made to the testing protocol as follows:
  1. In order to benchmark the performance of the olefin graft polymer systems, the test was modified to use a commercially available, mild, baby shampoo for all of the swatch washings, with the exception of one set.
  2. A set of tresses was, instead, washed with a commercially available shampoo claiming 45% color retention properties in a Level 3 application.

3. The color treatment was changed from Level 2 brown to Level 2 Intense Auburn.
4. The complete testing protocol included:
   a. Tresses washed with baby shampoo and treated with control conditioner;
   b. Tresses washed with baby shampoo and treated with a conditioner containing the polymer of Example 1;
   c. Tresses washed with baby shampoo and treated with the previous olefin graft conditioner;
   d. Tresses washed with the color retentive shampoo and treated with the control conditioner.

Figure 2:
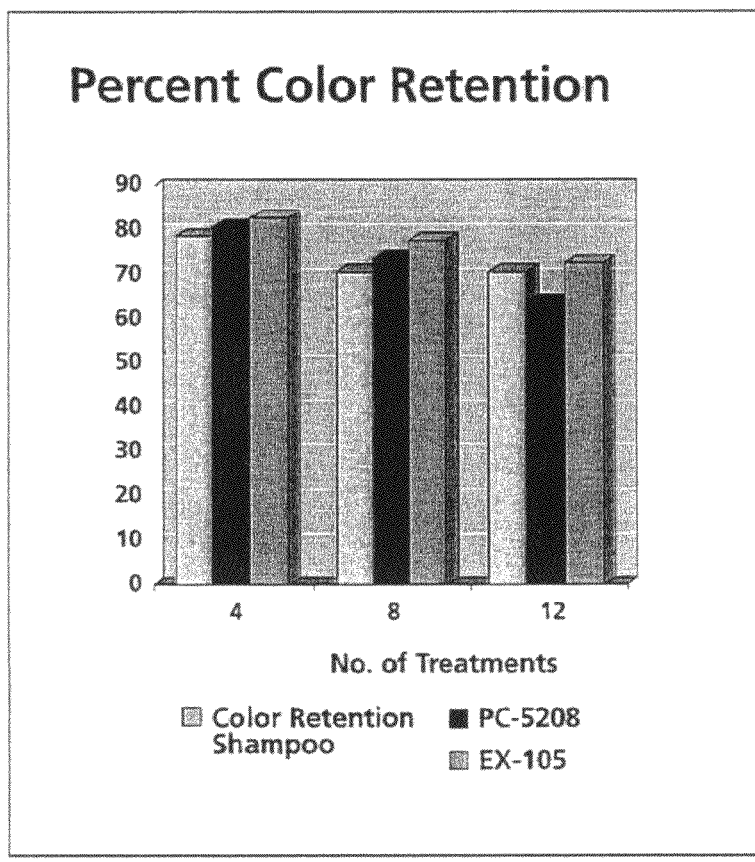
FIG. 2 is a bar plot of percent color retention as a function of number of treatments with a conditioner. Color-treated hair was subjected to treatment by an alternative formulation of a conditioner comprising a composition of the present invention as well as by a control formulation.

The drying cycle was also modified. After washing and treating with the conditioners, the swatches were combed with a wide tooth comb while being dried with a hair dryer on maximum setting. This was done for three (3) combings to eliminate excess conditioner and water. The swatches were then oven dried for 25 minutes at 40° C. If any residual moisture was evident at the end, then the hair dryer was used to finish moisture removal. The above cycle was repeated 12 times, with measurements taken at intervals of 4, 8, and 12. The hair samples were then evaluated for color loss using the same procedure as outlined above using the spectrophotometer. The resultant L*, a*, b*, values were measured and the Delta E calculated. A chart demonstrating the percent color retention is found in FIG. 2.

Figure 3:
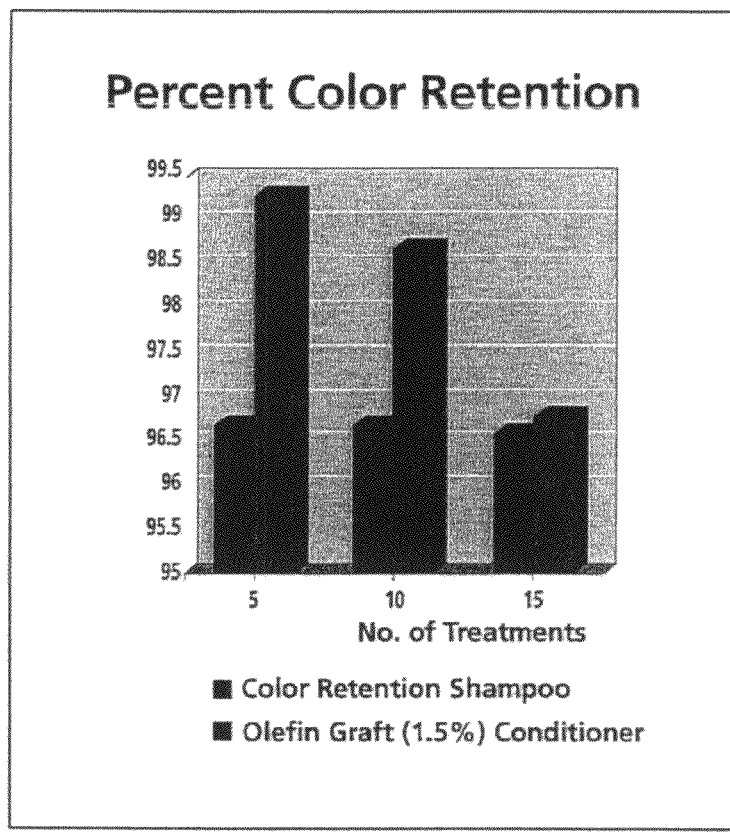
FIG. 3 is a bar plot of percent color retention as a function of number of treatments with a conditioner. Color-treated hair was subjected to treatment by another alternative formulation of an conditioner comprising a composition of the present invention as well as by a control formulation.

As one can tell, there was a significant increase in color retention with the revised test and protocol. It was important for us to notice the improved characteristics of the amino-modified olefin graft in comparison with the previously tested olefin graft. One of the observations made during the test concerned an increased combing effort on the olefin graft conditioners compared to the standard. We were concerned that damage to the hair or the protective barrier of the olefin graft was causing the drop in color retention as washings increased. In order to verify this, a third study was conducted in which the conditioning formula was modified to double the cetrimonium chloride while the olefin was cut to 1.5%. This was again tested against the commercial color retentive shampoo of the second study using the dark brown Level 2 color. The results of this study are found in FIG. 3.

Figure 4:
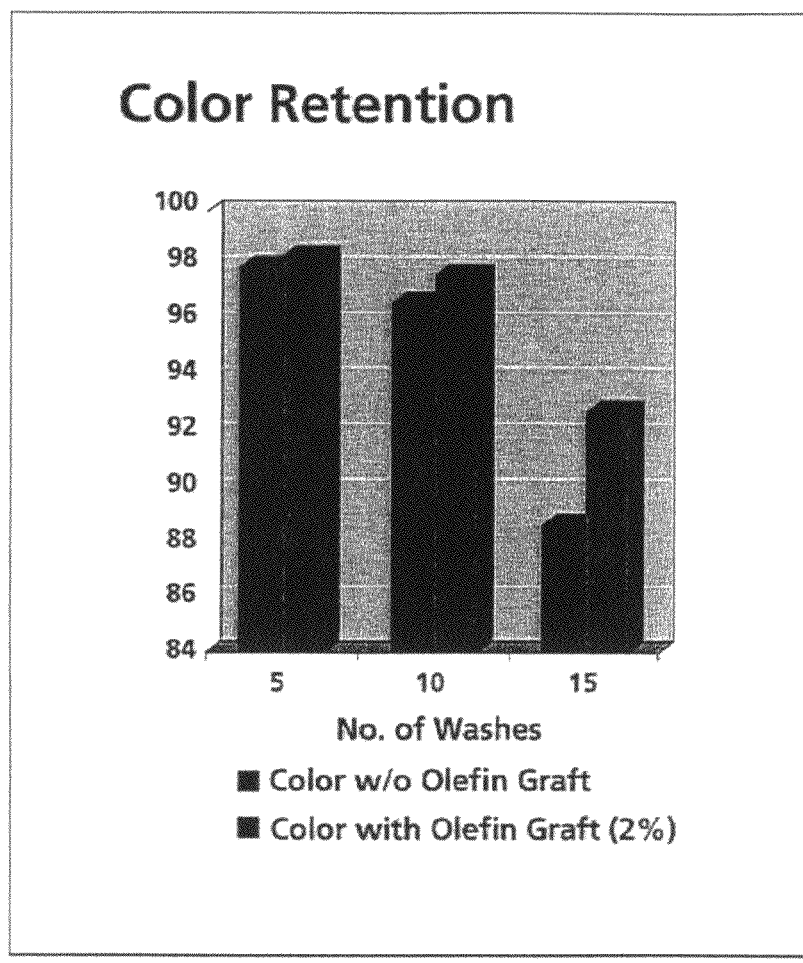
FIG. 4 is a bar plot of percent color retention as a function of number of treatments with a conditioner. Color-treated hair was subjected to treatment by still another alternative formulation of a conditioner comprising a composition of the present invention as well as by a control formulation.

In order to understand the potential effects of olefin polymers on hair color formulations, another method of incorporation was evaluated. To check the effects of the olefin polymer in the dye preparation, we prepared a commercial Level 3 hair dye preparation per the manufacturer's instructions. This dye preparation was split into equal parts. The graft polymer was added to one of the preparations at a 2% active level. The two dye preparations were then used to treat similar hair swatches per the manufacturer's instructions. These swatches were also measured for initial color and subjected to the same wash cycles using the commercial baby shampoo. This test indicates the amino modified olefin graft polymer can help retain color if the polymer application occurs in the coloring process. The results of the test are shown in FIG. 4. This method did not incorporate the use of a conditioner or other color-retention aid.

Example 6

The Composition of the Present Invention Boosts Sun Protection Factor

Polymers of this invention can, when manufactured with the appropriate monomers, provide SPF boosting properties in cosmetic formulations using organic UV absorbers. A creme formulation utilizing 3% of Syntran EX127, a polymer of this invention, gave a significant increase in SPF when compared to a similar SPF 15 skin creme without the olefin graft polymer. Tests were performed on a Labsphere Ultraviolet Transmittance Analyzer UV-1000S. The base skin creme formula is found in Table 7.

TABLE 7

| Ingredient | INCI Designation | Weight Percent |
| --- | --- | --- |
| Phase A/Heat to 75° C. | | |
| Distilled Water | | 59.07 |
| Dissolvine Na2S | | 0.05 |
| Propylene Glycol | Propylene Glycol | 2.00 |
| Phase B/Add @ 75° C. | | |
| Finsolv TN | | 3.00 |
| Protachem SMO | | 0.20 |
| Escalol 557 Octinoxate | | 7.50 |
| Escalol 567 Oxybenzone | | 3.00 |
| Escalol 587 | | 3.00 |
| Crodafos CES | | 4.00 |
| Ceterayl Alcohol 50/50 | | 4.00 |
| Crodafos C320 Acid | | 1.33 |
| Phase C/Add @ 60° C. | | |
| Olefin Graft Polymer Syntran EX127 | | 0.00 |
| Distilled Water | | 12.00 |
| Phase D/Add @ 45° C. | | |
| Liquid Germall Plus | | 0.60 |
| Frangrance | Frangrance | 0.15 |
| TEA 99% | | 0.10 |
| Total: | | 100.00 |

The SPF composition was prepared according to the following procedure: Heat A and B to 75° C. Add B to A with high shear agitation. Begin to cool and add Phase C at 60° C. Finish with Phase D at 45° C. Use TEA to raise pH to 6.5±0.5.

The Syntran EX127 containing creme is made from the same formula from Table 7 with adjustments made in water and pH control. (Table 8).

TABLE 8

| Ingredient | INCI Designation | Weight Percent |
| --- | --- | --- |
| Phase A/Heat to 75° C. | | |
| Distilled Water | | 61.00 |
| Dissolvine Na2S | | 0.05 |
| Propylene Glycol | Propylene Glycol | 2.00 |
| TEA 99% | | 0.10 |
| Phase B/Add @ 75° C. | | |
| Finsolv TN | | 3.00 |
| Protachem SMO | | 0.20 |
| Escalol 557 Octinoxate | | 7.50 |
| Escalol 567 Oxybenzone | | 3.00 |
| Escalol 587 | | 3.00 |
| Crodafos CES | | 4.00 |
| Ceterayl Alcohol 50/50 | | 4.00 |
| Crodafos C320 Acid | | 1.33 |
| Phase C/Add @ 60° C. | | |
| Olefin Graft Polymer Syntran EX127 | | 10.00 |
| Distilled Water | | 12.00 |
| Phase D/Add @ 45° C. | | |
| Liquid Germall Plus | | 0.60 |
| Frangrance | Frangrance | 0.15 |
| Total: | | 100.00 |

The control SPF 15 creme formulation was tested by Labsphere Transmittance Analyzer as having an SPF factor of 15.79. By the addition of 3% actives olefin graft polymer, the crème tested as having an SPF of 43.18. This was a 270% increase in SPF factor.

Example 7

Addition of Urethane to the Composition of the Present Invention Provides for Durable and Scuff-Resistant Coating for Keratinous Materials The present invention also relates to a urethane, acrylic, olefin graft polymer system which imparts a durable, scuff resistant coating to keratinous materials, especially as it pertains to fingernail enamels and coatings. This composition exhibits excellent water and solvent resistance with drying times equivalent to conventional solvent based nail enamels. The coating is comprised of an aqueous system composed of a urethane polymer, an acrylic polymer and an olefin graft polymer. The component polymers contain ionically charged functional groups that produce ionically cross-linked films with exceptional clarity and abrasion resistance. This invention also pertains to the balance of adhesive and cohesive properties obtained by the composition with improved dry time not normally found in water-based nail enamels.

The urethane of this invention is free from methylpyrrolidone, a potential mutagen, and when combined with the water-based acrylate form a more environmentally friendly nail enamel without the damaging side effects of solvent based systems. The strong urea and urethane groups form part of a substantial ionic attraction to both substrate and acrylic polymer. The acrylic polymer also contains both carboxyl and amino groups which help to interact in an association with the urethane to form a ionically bonded system approaching that of a covalently bonded system. Polymers of this composition are elucidated in U.S. Ser. No. 60/551,658, filed Mar. 9, 2004, the entire teachings of which are incorporated herein by reference. The olefin-graft polymer (U.S. Ser. No. 60/606,985, filed Sep. 3, 2004, the entire teachings of which are incorporated by reference) imparts a uniform distribution of olefin throughout the film allowing even wear with improved gloss. The strong ionic interaction between the highly functional polymers impart to films of this composition a rapid set and drying.

Formulations of this composition can vary by polymer ratios depending on the enamels market application. Urethane percentages can range from 5% to 80%; acrylic polymer from 5% to 90%; and the olefin graft 1% to 20%. Optionally, copolymers of ethylene and/or propylene can be utilized to modify the scuff resistance. Formulations require a minimum of plasticizer and coalescent due to the ionic quick set.

A representative formulation of this invention can be described as follows:

|  | Formulation Weight |
|---|---|
| Co-Solvent Free, water-based Aliphatic Urethane* @ 38% | 15.75 |
| Bimodal Polymer @ 40%** | 19.74 |
| Olefin-Graft polymer @ 38%*** | 2.0 |
| Oxidized Polyethylene polymer @ 40% | 1.1 |
| Coalescent (Optional): | |
| Dibutyl Maleate | 0.5 |
| Propylene Glycol mono methyl ether | 0.9 |

| Preliminary Test results: | | |
|---|---|---|
|  | Invention Disclosure | Solvent Enamel |
| Rub Test (Ethyl Alcohol) | 5 | 4 |
| Water Resistance (One hour water spot) | 5 | 5 |
| Gloss | 5 | 4.5 |
| Dry Time (Surface Tack with Cotton) | 5 | 5 |
| Odor | 5 | 1 |
| (Test Measurement: 1 to 5; 5 the best) | | |

*n-Methyl Pyrrolidone (NMP) or co-solvent essentially free or free of aliphatic polyester polyurethane dispersion.
**The Acrylic Bimodal polymer is comprised of two distinct polymer chains copolymerized by free-radical polymerization in a water-based system. One chain contains anionic functionality from either methacrylic acid, acrylic acid or a combination of both. The second polymer chain contains simple amino esters of methacrylic acid or methacrylamide. The remaining monomer composition of both polymer chains is comprised of lower alkyl (C1 to C8) esters of both methacrylic and acrylic acid.
***The Olefin Graft polymer is a copolymer of ethylene/acrylic acid copolymer grafted in a water-based system with lower alkyl esters (C1 to C8) of both acrylic and methacrylic acid and styrene.

As used herein, the term "bimodal" describes polymer compositions that include two polymers, one having anionic character and one having cationic character.

EQUIVALENTS

While this invention has been particularly shown and described with references to preferred embodiments thereof, it will be understood by those skilled in the art that various changes in form and details may be made therein without departing from the scope of the invention encompassed by the appended claims.

What is claimed is:

1. A polymer emulsion for use in a cosmetic composition, comprising:
    a first copolymer that is a copolymer of ethylene and acrylic acid;
    a second copolymer that includes two or more monomer units selected from the group consisting of an acrylic acid, methacrylic acid, ethyl acrylate, butyl acrylate, 2-ethyl hexyl acrylate, butyl methacrylate, methyl methacrylate, styrene, a ($C_1$-$C_6$) aminoalkyl ester of methacrylic acid or acrylic acid or a quaternized adduct thereof, a polyethylene glycol (PEG) modified acrylate or methacrylate, and a polypropylene glycol (PPG) modified acrylate or methacrylate, said PEG modified or PPG modified acrylate or methacrylate having 1-10 moles of ethylene oxide or propylene oxide per 1 mole of acrylic or methacrylic acid; and
    a resin, distinct from the second copolymer, the resin having an average molecular weight from about 500 to about 15,000 daltons, wherein the resin includes two or more monomer units selected from the group consisting of a ($C_1$-$C_6$) ester of methacrylic acid or acrylic acid, methacrylic acid, a polyethylene glycol (PEG) or a polypropylene glycol (PPG) modified acrylate or methacrylate, said PEG modified or PPG modified acrylate or methacrylate having 1-10 moles of ethylene oxide or propylene oxide per 1 mole of acrylic or methacrylic acid.

2. The polymer emulsion of claim 1, further including:
    at least one stabilizing emulsifier.

3. The polymer emulsion of claim 1, further including:
    a polymer selected from the group consisting of an oxidized polyethylene polymer and an oxidized polypropylene polymer, said oxidized polyethylene polymer and oxidized polypropylene polymer including a cationic moiety.

4. The polymer emulsion of claim 2, wherein the stabilizing emulsifier is selected from the group consisting of sodium lauryl sulfate, sodium lauryl ether sulfate, a sulfonated ($C_1$-$C_{15}$)mono or ($C_1$-$C_{15}$)dialkyl ester of succinic acid or a salt thereof, a ($C_1$-$C_{20}$) alkyl ester of diphenyl oxide, a ($C_{10}$-$C_{30}$) alkyl alcohol ethoxylate, and an ethylene oxide-propylene oxide block polymer.

5. The polymer emulsion of claim 4, wherein the stabilizing emulsifier is selected from the group consisting of a ($C_{10}$-$C_{30}$) alkyl alcohol ethoxylate, and an ethylene oxide-propylene oxide block polymer.

6. The polymer emulsion for use in a cosmetic composition, comprising:
- a first copolymer that is a copolymer of ethylene and acrylic acid;
- a second copolymer that includes two or more monomer units selected from the group consisting of an acrylic acid, methacrylic acid, ethyl acrylate, butyl acrylate, 2-ethyl hexyl acrylate, butyl methacrylate, methyl methacrylate, styrene, a ($C_1$-$C_6$) aminoalkyl ester of methacrylic acid or acrylic acid or a quaternized adduct thereof, a polyethylene glycol (PEG) modified acrylate or methacrylate, and a polypropylene glycol (PPG) modified acrylate or methacrylate, said PEG modified or PPG modified acrylate or methacrylate having 1-10 moles of ethylene oxide or propylene oxide per 1 mole of acrylic or methacrylic acid;
- at least one stabilizing emulsifier;
- a resin, distinct from the second copolymer, the resin having an average molecular weight from about 500 to about 15,000 daltons, wherein the resin includes two or more monomer units selected from the group consisting of a ($C_1$-$C_6$) ester of methacrylic acid or acrylic acid, methacrylic acid, styrene, a polyethylene glycol (PEG) or a polypropylene glycol (PPG) modified acrylate or methacrylate, said PEG modified or PPG modified acrylate or methacrylate having 1-10 moles of ethylene oxide or propylene oxide per 1 mole of acrylic or methacrylic acid;
- a polymer selected from a group consisting of an oxidized polyethylene polymer, and an oxidized polypropylene polymer, said oxidized polyethylene polymer and oxidized polypropylene polymer including a cationic moiety.

7. The polymer emulsion of claim 6, wherein the stabilizing emulsifier is selected from the group consisting of sodium lauryl sulfate, sodium lauryl ether sulfate, a sulfonated ($C_1$-$C_{15}$)mono or ($C_1$-$C_{15}$)dialkyl ester of succinic acid or a salt thereof, a ($C_1$-$C_{20}$) alkyl ester of diphenyl oxide, a ($C_{10}$-$C_{30}$) alkyl alcohol ethoxylate, and an ethylene oxide-propylene oxide block polymer.

8. The polymer emulsion of claim 7, wherein the stabilizing emulsifier is selected from the group consisting of a ($C_{10}$-$C_{30}$) alkyl alcohol ethoxylate, and an ethylene oxide-propylene oxide block polymer.

9. The polymer emulsion of claim 6, comprising:
- 30% to 99% by weight of the first copolymer;
- 1% to 70% by weight of the second copolymer;
- 1% to 15% by weight of the stabilizing emulsifier;
- 0.2% to 20% by weight of the resin; and
- 0.5% to 5.0% by weight of the polymer selected from the group consisting of an oxidized polyethylene polymer, and an oxidized polypropylene polymer, said oxidized polyethylene polymer and an oxidized polypropylene polymer including a cationic moiety.

10. The polymer emulsion of claim 6, having an average molecular weight in the range of 2000-1,000,000 daltons.

11. A personal care fixative comprising a polymer emulsion of claim 6.

12. The personal care fixative of claim 11 further including one or more volatile solvents.

13. The personal care fixative of claim 12 having a total volatile solvent concentration ranging from about 30 to about 95 weight percent.

14. The personal care fixative of claim 11 further including a neutralizing agent.

15. The personal care fixative of claim 11 further including an alcohol.

16. The personal care fixative of claim 11 further including at least one component selected from the group consisting of a thickening agent, a dispersing agent, an emulsifier, an emollient, a stabilizer, a surfactant, a fragrance, a preservative, a protein, a conditioner, a colorant, a dye, a plasticizer, a neutralizer, a glossifier, and a propellant.

17. The polymer emulsion of claim 1, wherein the resin includes a ($C_1$-$C_6$) ester of methacrylic acid or acrylic acid selected from ethyl acrylate, butyl acrylate, butyl methacrylate, or methyl methacrylate.

18. The polymer emulsion of claim 6, wherein the resin includes a ($C_1$-$C_6$) ester of methacrylic acid or acrylic acid selected from ethyl acrylate, butyl acrylate, butyl methacrylate, or methyl methacrylate.

* * * * *